United States Patent
Jabar, Jr.

(10) Patent No.: US 6,844,181 B2
(45) Date of Patent: Jan. 18, 2005

(54) METHOD OF INHIBITING FUNGAL GROWTH

(75) Inventor: Anthony Jabar, Jr., Waterville, ME (US)

(73) Assignee: Global Protein Products, Inc., Winslow, ME (US)

( * ) Notice: Subject to any disclaimer, the term of this patent is extended or adjusted under 35 U.S.C. 154(b) by 149 days.

(21) Appl. No.: 10/150,500

(22) Filed: May 17, 2002

(65) Prior Publication Data

US 2003/0004114 A1 Jan. 2, 2003

Related U.S. Application Data

(60) Provisional application No. 60/291,921, filed on May 18, 2001.

(51) Int. Cl.⁷ .................................................. C12N 1/12
(52) U.S. Cl. .................................................. 435/252.1
(58) Field of Search ....................... 435/252.1; 426/573, 426/656; 530/300, 350

(56) References Cited

U.S. PATENT DOCUMENTS

| | | | |
|---|---|---|---|
| 4,277,469 A | | 7/1981 | Worthington |
| 4,902,920 A | | 2/1990 | Wolaver ..................... 307/514 |
| 5,376,391 A | | 12/1994 | Nisperos-Carriedo et al. |
| 5,591,473 A | * | 1/1997 | McArdle .................... 426/573 |
| 5,645,880 A | | 7/1997 | McArdle |
| 5,747,416 A | | 5/1998 | McArdle |
| 5,942,123 A | | 8/1999 | McArdle |
| 6,192,094 B1 | | 2/2001 | Herrmann et al. .......... 375/375 |

FOREIGN PATENT DOCUMENTS

| | | |
|---|---|---|
| EP | 0991193 A1 | 5/2000 |
| WO | WO-01/33828 A2 | 5/2001 |

* cited by examiner

*Primary Examiner*—Karen Cochrane Carlson
*Assistant Examiner*—Sheridan K Snedden
(74) *Attorney, Agent, or Firm*—Nixon Peabody LLP

(57) ABSTRACT

The present invention provides a method of inhibiting fungal growth on a growing plant of agricultural or horticultural origin. In a preferred embodiment, an effective amount of a fungal growth inhibiting composition comprising a peptide and a polysaccharide is administered to the plant.

15 Claims, No Drawings

METHOD OF INHIBITING FUNGAL GROWTH

The present invention claims the benefit of U.S. Provisional Application No. 60/291,921, filed May 18, 2001, the disclosure of which is incorporated herein by reference.

BACKGROUND OF THE INVENTION

1. Field of the Invention

The present invention relates to methods and compositions used to protect growing plants from fungal diseases.

2. Technical Background

As a result of increasing concern over environmental safety of non-degradable synthetic products and food safety, there is a demand for natural degradable products as alternatives for protecting agricultural products both during and after growth season from a variety of environmental pathogens.

The protection of desirable plants and their produce from fungal pathogen infection has traditionally required preventative applications of fungicidal agents. Fungicidal compounds have long been used to increase yields and extend agricultural production capabilities into new areas. They have also been extremely important tools for ameliorating season-to-season differences in yield and quality caused by weather-driven variations in disease pressure.

The future role of fungicides in agriculture is increasingly threatened by several factors including the development of pest resistance, increasing concerns about food safety, and environmental accumulation of toxic compounds. As older fungicides are removed from the market due to regulatory changes, and new fungicides are becoming increasingly expensive to register, there is an increasing need to find ways to more wisely use the remaining, safest fungicides. This is particularly true for the many crop/disease combinations which do not represent large enough markets to pay for the cost of new compound registration. Wiser fungicide use will include ways to reduce application rates (and thus potential residues), finding ways to extend registrations to new crops, and identifying new fungicidal compositions and treatments to combat the development of pest resistance.

Chemical fungicides have provided an effective method of control; however, the public has become concerned about the amount of residual chemicals which might be found in food, ground water and the environment. Stringent new restrictions on the use of chemicals and the elimination of some effective pesticides from the market place could limit economical and effective options for controlling fungal growth.

The commercialization of disease biocontrol agents has been hampered by inconsistent field performance. Organisms which show biocontrol potential in laboratory and greenhouse experiments often fail to compete with the existing microflora when applied outdoors and are thus unable to express their biocontrol potential, regardless of mode of action. Specifically there is a need for disease control methods which are more compatible with the need for affordable and effective disease control, a high degree of food safety, and minimal environmental impact.

One example of fungal infection during the growth season of grapes is powdery mildew caused by *Uncinula necator*. Infection can result in severe damage even in dry areas such as California. Traditionally this disease was controlled with applications of elemental sulfur, but this necessitates frequent, high volume applications of an irritating material. The introduction of egosterol biosynthesis inhibiting fungicides (primarily triazoles) greatly simplifies control, but also selects for tolerant strains. Some of these compounds are also known to have potential teratogenic effects and very long soil residuals. In these and other examples, alternative control methods are in great demand—particularly methods which are safer or more environmentally benign.

A new class of peptide-polysaccharides has been recently introduced. McArdle in U.S. Pat. Nos. 5,942,123, 5,747,416, 5,645,880, discloses these peptide-polysaccharides for a number of uses. However, there has been no suggestion or recognition of their use as inhibiting fungal growth on plants during the growth season.

SUMMARY OF THE INVENTION

It is an object of this invention to provide a method of inhibiting fungal growth that is nontoxic and biodegradable, and has a minimal impact on worker safety and the environment.

In one embodiment, the present invention provides a method of inhibiting fungal growth on growing plants of agricultural and horticultural origin, including fruits. The term "plant" or "plants," as used herein, also includes the term "fruit" or "fruits." The fruit or fruits, as used herein, means the reproductive product of a plant, the seed of plants, or the part that contains the seeds including the edible, juicy product of a plant, which usually covers the seeds, or the matured ovary of a plant, consisting of the seeds and their pericarp (coating) and including whatever may be incorporated with it. The term "fruit" entails any product of vegetable growth useful to humans or animals, for example, grapes, figs, corn, cotton, flax, and all cultivated plants. Other examples of the fruit include, but are not limited to apples, apricots, avocados, bananas, cherries, coconuts, dates, grapes, guava, lychee, mangoes, melons, nectarines, papaya, peaches, pears, persimmons, pineapples, plantains, plums, pomegranates, prunes, stone fruit, strawberries, tomatoes, blueberries, raspberries, blackberries, and citrus fruits, such as grapefruit, oranges, lemons, limes, clementines and tangerines.

The preferred method of the present invention involves administering to growing plants a composition comprising a peptide and a polysaccharide in an amount effective to inhibit fungal growth. Preferably, the plant is one susceptible to fungal infectional. In the composition, the peptide is present in an amount of 2–90% by weight of the dry peptide-polysaccharide complex, and the polysaccharide is present in an amount of 10–98% by weight of the dry peptide-polysaccharide complex. In a preferred embodiment, the peptide is present in an amount of 2–30% by weight of the dry peptide-polysaccharide complex, and the polysaccharide is present in an amount of 70%–98% by weight of the dry peptide-polysaccharide complex. The administration may be performed any time during the growth of the plant or fruit and can be applied one or more times during the growth season.

The peptide for use in the composition can be obtained from natural, recombinant or synthetic sources. Preferably, the natural source is of plant origin including maize, rice, tobacco, alfalfa, wheat, barley, soybean, and peanuts. A preferred plant peptide is zein. Alternatively, the peptide can be isolated from animal sources including milk, eggs, animal epidermal tissue, or animal connective tissue.

The polysaccharide for use in the composition can be obtained from natural, recombinant or synthetic sources. Preferably the polysaccharide is a cellulosic derivative.

Preferred cellulosic derivatives include carboxymethylcellulose, methylcellulose, hydroxypropyl cellulose, hydroxypropyl methylcellulose, and microcrystalline cellulose.

In another embodiment, the polysaccharide is starch or a starch derivative. Starch or starch derivatives include, for example, tapioca starch, potato starch, rice starch, wheat starch. Modified versions may also be used and include, for example, pregelatinized starch, oxidized starch, ethylated starch, starch dextrins, or maltodextrin.

In a further embodiment, the polysaccharide is pectin. The polysaccharide may be from seaweed and can include, for example, agar, alginate, carrageenan and fucellaran.

In another embodiment, the polysaccharide is derived from an exudate gum polysaccharide and, can include, for example, gum arabic, gum ghatti, gum karaya, and gum tragacanth.

The polysaccharide may be derived from seed gum such as guar gum or locust bean gum. Alternatively, the polysaccharide is derived from microbial fermentation and includes, for example, xanthan gum or gellan gum. Guar gum may be used. In the preferred embodiment, the polysaccharide is guar gum, gum arabic, carrageenan, alginates, or any cellulose.

Preferred polysaccharides include cellulose, guar gum, gum arabic, carrageenan, and alginates.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed.

DESCRIPTION OF THE PREFERRED EMBODIMENTS OF THE INVENTION

The present invention provides a method of inhibiting fungal growth on a growing plant of agricultural or horticultural origin. In a preferred embodiment, an effective amount of a fungal growth inhibiting composition comprising a peptide and a polysaccharide is administered to the plant. In the composition, the peptide is present in an amount of 2–90% by weight of the dry peptide-polysaccharide complex and the polysaccharide is present in an amount of 10–98% by weight of the dry peptide-polysaccharide complex. Preferably, the peptide is present in an amount of 2–30% by weight of the dry peptide-polysaccharide complex and the polysaccharide is present in an amount of 70%–98% by weight of the dry peptide-polysaccharide complex.

The administration of the composition may be performed at any time during the growth of the plant or fruit either once or several times during the growth season. In the preferred embodiment, the administration is performed several times during the growth season. The administration of the composition can be carried out by any means used in the art, e.g., spraying the composition onto the growing plants.

The composition for use in the present invention includes at least one peptide and at least one polysaccharide. In the composition, the peptide is present in an amount of 2–90% by weight of the dry peptide-polysaccharide complex and the polysaccharide is present in an amount of 10–98% by weight of the dry peptide-polysaccharide complex. Preferably, the peptide is present in an amount of 2–30% by weight of the dry peptide-polysaccharide complex and the polysaccharide is present in an amount of 70%–98% by weight of the dry peptide-polysaccharide complex.

The peptide can be obtained from any natural, recombinant/transgenic, or synthetic source. Natural sources include peptides produced by naturally occurring organisms or hybrids of naturally occurring organisms. Transgenic/recombinant sources include but are not limited to organisms produced through genetic engineering. Synthetic sources include peptides produced by artificial chemical synthesis.

The natural peptide sources include, but are not limited to, maize, rice, tobacco, alfalfa, wheat, barley, soybean, peanuts, milk, eggs, animal epidermal tissue, animal connective tissue, etc. Peptides of plant origin are preferred and include, but are not limited to, corn gluten, corn zein, wheat gliadin, wheat glutenin, wheat gluten, barley hordein, soy protein, soy protein isolates, peanut protein. In certain embodiments, peptides of animal origin can be used and include, but are not limited to, keratin, collagen, gelatin, whey protein, casein, and egg albumin. In a preferred embodiment of the present invention the peptides are zein, corn gluten, gliadin, glutenin, wheat gluten, barley hordein, soy protein, whey protein, casein, or mixtures thereof.

The polysaccharides utilized in the present invention are, in particular, hydrocolloid polysaccharides derived from plant, animal or microbial sources. Polysaccharides useful in the present invention include, but are not limited to, cellulosic derivatives such as carboxymethylcellulose, methylcellulose, hydroxypropyl cellulose, hydroxypropyl methylcellulose, microcrystalline cellulose, etc., starches and derivatives including, but not limited to, corn starch, tapioca starch, potato starch, rice starch, wheat starch, and modified versions thereof such as pregelatinized starch, oxidized starch, ethylated starch, starch dextrins, maltodextrin, etc. Additional polysaccharides useful in the present invention include, but are not limited to, pectin, polysaccharides derived from seaweed such as agar, alginates, carrageenan, and fucellaran, exudate gum polysaccharides such as gum arabic, gum ghatti, gum karaya, and gum tragacanth, seed gums such as guar gum and locust bean gum, polysaccharides derived from microbial fermentation such as xanthan gum and gellan gum, and nitrogen containing polysaccharides such as chitosan. Polysaccharides of the type described herein produced by transgenic organisms can also be useful in the present invention. In a preferred embodiment of this invention, the polysaccharides are guar gum, starch dextrins, pectin, gum arabic, and mixtures thereof.

The total peptide-polysaccharide composition is defined as the total weight of the peptide and the polysaccharide. The peptide is present in an amount between about 2% and 90% by weight of the peptide-polysaccharide composition, preferably in the amount ranging between about 5% and 30%.

The polysaccharide is present in an amount between 10% and 98% by weight of the total peptide-polysaccharide composition, preferably in the amount ranging from 70% to 95%. The total peptide-polysaccharide composition is defined as the total weight of the peptide and the polysaccharide.

To prepare the composition, the peptide is first dissolved or dispersed in an appropriate solvent. The solvent can be an aqueous system or an organic solvent based system depending on the solubility parameters of the peptide. In a preferred embodiment of this invention the peptide, zein, is dissolved in a water/alcohol solution containing a ratio of water to alcohol of 30/70 by volume to form a solution of peptide in aqueous alcohol. The polysaccharide is subsequently added to the peptide aqueous alcohol solution thereby forming a peptide-polysaccharide complex in aqueous alcohol. The peptide-polysaccharide complex solution can then be dried to a free flowing powder using conventional drying or evaporation equipment; however it may be preferable to maintain the peptide-polysaccharide complex in solution for certain applications.

In another embodiment, to prepare the composition, a solution of peptide is dissolved in an appropriate solvent, which is capable of dissolving the peptide. The solution is filtered to remove the non-peptide material. The polysaccharide is added to the filtered peptide solution. The peptide-polysaccharide solution is then dried by conventional methods with care not to exceed 140° C. Conventional drum drying, spray drying, or oven drying is easily accomplished utilizing commercially available equipment. The dried powder is then ground to an appropriate size making it thereby re-dispersible in solution.

In an alternative embodiment, the composition can be prepared by blending a dry peptide with a dry polysaccharide. This dry blending can be carried out in conventional dry blending equipment.

The peptide-polysaccharide dry flowable powder compositions made according to the methods above are then applied to the plant or fruit by conventional application equipment. For example, a spray rig is a commercially available method to administer the composition.

Examples of the fungi that can be treated include, but are not limited to, black rot caused by the fungus *Guignardia bidwellii,* downy mildew caused by *Plamopara viticola,* powdery mildew caused by *Uncinula necator,* eutypa dieback, caused by the fungus *Eutypa armeniacae,* and phomopsis leaf and cane spot disease caused by the fungus *Phomopsis viticola.*

A preferred effective fungal growth inhibiting amount of the composition is between 0.25 to 5.0 lbs per acre.

Alternatively, the peptide-polysaccharide composition can be re-dispersed in water or other appropriate solvent, with or without the aid of conventional dispersants, emulsifiers or solubilizing agents, and applied to the plant or fruit as a solution. For example, spray equipment may be used to apply the peptide-polysaccharide solution.

Advantageously, additives may be added to the aqueous alcohol solution to promote stability of the peptide-polysaccharide complex. Additives include, but are not limited to, solubilizing agents such as glycol, propylene glycol, or other low molecular weight alcohols; surfactants such as alkylpolyglucosides, fatty alcohols, fatty acids, or alkylbenzenesulfonates and dispersants; emulsifiers such as lecithin or sorbitan monooleate; pH control agents such as mineral acids and their salts, organic acids and their salts, bases, both organic and inorganic; buffers such as phosphates, acetates and carbonates; anti-microbial compounds such as BHT, methyl or propylparaben, benzoic acid, sorbic acid, propionic acid and their salts; chelating agents such as EDTA, MEA or TEA; and other such additives generally known or apparent to those skilled in the art.

The composition can be effectively used to treat growing plants either by a one-time application or, alternatively, the composition may be administered several times during the growth season.

The peptide-polysaccharide compositions can be admixed with inert agents, bulking agents, or diluent materials in order to uniformly distribute the peptide-polysaccharide onto the plant. Materials which can be used in the present invention include, but are not limited to clay, talc, limestone, quick lime, silica, hydrated silica, bentonite, salts of organic acids, organic acids, surfactants, dispersants, emulsifiers, solvents, ash, composted materials, tree bark, and mixtures thereof. When admixing these materials care should be taken to ensure that the appropriate amount of peptide-polysaccharide is distributed uniformly onto the plant or fruit.

The invention will be further clarified by the following example which are intended to be exemplary of the invention.

EXAMPLE

Wine Grape Vineyard—Kenwood, Calif.

A quarter acre plot with approximately 200 vines of chardonnay wine grapes was treated with a composition containing a peptide-polysaccharide composition. To prepare the composition, zein (Freeman Industries, Tuckahoe, N.Y.) was dissolved in a water/alcohol solution containing a ratio of water to alcohol of 30/70 by volume to form a solution of zein in aqueous alcohol. The guar gum (Monson Chemical, Leominster, Mass.) was subsequently added to the peptide aqueous alcohol solution thereby forming a peptide-polysaccharide complex in aqueous alcohol. The peptide-polysaccharide complex was then dried to a free flowing powder using conventional air flow drying. A peptide-polysaccharide complex composed of 8% zein/92% guar gum dry flowable powder was prepared. The composition was dispersed in water at a concentration of 0.4% and applied to grape vines at a rate of 1.5 lbs/acre. The application schedule began in early May once three inches of new growth was observed on the vine, and treatments continued every 12–16 days until two weeks before harvest for a total of 8 treatments. The treatment was evaluated against Thiolux, a conventional sulfur treatment. The treatment was designed to provide resistance to powdery mildew, a common mold found in vineyards of the west coast, including California. Infestation of powdery mildew causes poor grape quality, lower yields, and ultimately lower quality wine.

Visual observations were continually made throughout the growing season for the presence of powdery mildew on the canes, shoots, leaves and fruit.

No visible differences were noted in the occurrence of powdery mildew throughout the growing season compared to the control group. The harvested grapes were of good size, color, and quality.

The preceding example is to be evaluated as illustrative and are not intended to limit the scope of this invention.

It is also to be understood that the following claims are intended to cover all of the generic and specific features of the invention herein described and all statements of the scope of the invention which, as a matter of language might be said to fall there between. Particularly, it is to be understood that in said claims, ingredients or compounds recited in the singular are intended to include compatible mixtures of such ingredients wherever sense permits.

I claim:

1. A method of inhibiting fungal growth on a growing agricultural or horticultural plant comprising the steps of:
   a. identifying a growing plant susceptible to or having fungal growth; and
   b. contacting said growing plant with an effective amount of a fungal growth inhibiting composition comprising a peptide and a polysaccharide, wherein the peptide is present in an amount of 2–90% by weight of the composition and the polysaccharide is present in an amount of 10–98% by weight of the composition.

2. The method of claim 1, wherein the peptide is present in an amount of 2–30% by weight of the composition and the polysaccharide is present in an amount of 70%–98% by weight of the composition.

3. The method of claim 1, wherein the peptide is isolated from a natural, recombinant or synthetic source.

4. The method of claim 1, wherein the peptide is zein.

5. The method of claim 1, wherein the polysaccharide is obtained from a natural, recombinant or synthetic source.

6. The method of claim 5, wherein the polysaccharide is a cellulosic derivative.

7. The method of claim 6, wherein the cellulosic derivative is selected from a group consisting of carboxymethylcellulose, methylcellulose, hydroxypropyl cellulose, hydroxypropyl methylcellulose, and microcrystalline cellulose.

8. The method of claim 1, wherein the polysaccharide is starch or a starch derivative.

9. The method of claim 1, wherein the polysaccharide is pectin.

10. The method of claim 1, wherein the polysaccharide is derived from an exudate gum polysaccharide.

11. The method of claim 1, wherein the polysaccharide is cellulose, guar gum, gum arabic, carrageenan, and alginates.

12. The method of claim 1, wherein the plant is a grape vine.

13. The method of claim 1, wherein the growing agricultural plant is fruit bearing.

14. The method of claim 13, wherein the fruit is a grape.

15. The method of claim 13, wherein the fruit is contacted with the composition.

* * * * *